United States Patent
Shimkets (10) Patent No.: US 7,259,144 B2
(45) Date of Patent: Aug. 21, 2007

(54) METHODS FOR DIAGNOSING AND TREATMENT OF HYPERPHOSPHATEMIC CONDITIONS USING FGF20 POLYPEPTIDES

(75) Inventor: Richard A. Shimkets, Guilford, CT (US)

(73) Assignee: CuraGen Corporation, New Haven, CT (US)

( * ) Notice: Subject to any disclaimer, the term of this patent is extended or adjusted under 35 U.S.C. 154(b) by 388 days.

(21) Appl. No.: 10/644,349

(22) Filed: Aug. 20, 2003

(65) Prior Publication Data

US 2005/0032073 A1 Feb. 10, 2005

Related U.S. Application Data

(60) Provisional application No. 60/449,293, filed on Feb. 21, 2003.

(51) Int. Cl.
*A61K 38/18* (2006.01)
*C07K 14/50* (2006.01)

(52) U.S. Cl. .......................................... 514/12; 530/399
(58) Field of Classification Search ...................... None
See application file for complete search history.

(56) References Cited

FOREIGN PATENT DOCUMENTS

WO    WO 00/60085    10/2000

OTHER PUBLICATIONS

Jeffers, M., R. Shimkets, et al. (2001). "Identification of a novel human fibroblast growth factor and characterization of its role in oncogenesis." Cancer Res 61(7): 3131-8.
Kirikoshi, H., N. Sagara, et al. (2000). "Molecular cloning and characterization of human FGF-20 on chromosome 8p21.3-p22." Biochem Biophys Res Commun 274(2): 337-43.
The ADHR Consortium, Nature Genetics, vol. 26:345-348 (2000).
Hafdi et al., Biochem. J., vol. 320:615-621 (1996).
Hughes, J. Histochem. & Cytochem., vol. 45(7):1005-1019 (1997).
Klint and Claesson-Welsh, Frontiers in Bioscience, vol. 4:d165-177 (1999).
NCBI Entrez Protein Database, Accession No. O15520 (updated Jul. 11, 2006).
NCBI Entrez Protein Database, Accession No. P31371 (updated Jun. 13, 2006).
NCBI Entrez Protein Database, Accession No. Q9NP95 (updated Apr. 18, 2006).
Ornitz et al, J. Biol. Chem., vol. 271(25):15292-15297 (1996).
Powers et al., Endocrine-Related Cancer, vol. 7:165-197 (2000).
Shimada et al., Proc. Natl. Acad. Sci., vol. 98(11):6500-6505 (2001).

*Primary Examiner*—Christine J. Saoud
(74) *Attorney, Agent, or Firm*—Mintz, Levin, Cohn, Ferris, Glovsky and Popeo, P.C.; Ivor R. Elrifi, Esq.

(57) ABSTRACT

The present invention describes novel methods for diagnosis and treatment of conditions that alter phosphate transport in mammals. The fibroblast growth factor proteins and nucleotides that may be useful as a therapeutic or in the diagnosis of such conditions are also described.

9 Claims, 9 Drawing Sheets

* significant inhibition by PD vs. FGF alone

C.

* significant inhibition by SB vs. FGF alone

METHODS FOR DIAGNOSING AND TREATMENT OF HYPERPHOSPHATEMIC CONDITIONS USING FGF20 POLYPEPTIDES

RELATED APPLICATIONS

This application claims the benefit of priority from U.S. Provisional Application U.S. Ser. No. 60/449293, filed Feb. 21, 2003.

FIELD OF THE INVENTION

Phosphorus is a major component of bone, the most abundant intracellular anion, and among the most abundant tissue constituents. It is critical to and involved in nearly all metabolic processes. The total amount of phosphorus in the normal adult is between 700 and 1,000 grams, of which approximately 85% is found in the skeleton, 15% is found in soft tissues, and 0.1% is found in extracellular fluids. In fasting plasma, most of the phosphorus is present as inorganic orthophosphate in concentrations of 2.8 to 4.0 mg/dl.

In the body, adsorption of phosphorus is under the influence of vitamin D, while phosphorus excretion is under the control of parathyroid hormone (Parathyroid hormone decreases tubular phosphate reabsorption and increases excretion of soluble phosphorus into the urine). The effect of vitamin D on phosphate reabsorption is relatively minor. The concentration of phosphorus in mammals is affected by various factors including age, diet, a large number of pharmaceutical products, and diurnal variations. It is essential for the interpretation of serum levels and urinary clearances that samples be obtained in the fasting state upon which clinical values have been determined and standardized.

Hypophosphatemia has many causes including decreased dietary intake of phosphorus-containing foods, decrease in intestinal absorption, increased excretion into the urine, renal failure, and medications. Unfortunately, the finding of hypophosphatemia is not a reliable indicator of deficiency, since total-body deficiency of phosphorus may be found in a patient's with hyperphosphatemia with, for example, diabetic ketoacidosis.

Hypophosphatemia may be moderate to severe. A common cause of the condition is respiratory alkalosis, and discovery of hypophosphatemia is often the first clinical sign for serious causes of hyperventilation such as sepsis or otherwise unsuspected alcohol withdrawal. Other causes may be phosphorylation of glucose intermediates that may cause cellular uptake of phosphorus with resulting hypophosphatemia. Other common causes of hypophosphatemia include the administration of insulin and consumption of nutrients that stimulate insulin release. Cellular phosphorus uptake also takes place in patients recovering from hypothermia as a result of reactivating metabolism in the patient. Certain malignancies such as fibrosarcomas, prostatic cancers, and possibly small cell cancers of the lung have been reported as additional causes. Still other causes of such hypophosphatemic disorders, specifically hereditary disorders of isolated phosphate wasting, are those such as X-linked hypophosphatemic rickets (XLH), hypophosphatemic bone disease (HBD), hereditary hypophosphatemic rickets with hypercalciuria (HHRH) and autosomal dominant hypophosphatemic rickets (ADHR). ADHR is characterized by low serum phosphorus concentrations, rickets, osteomalacia, lower extremity deformities, short stature, bone pain and dental abscesses.

Severe hypophosphatemia is defined as phosphorus levels in serum below 1.0 mg/dL, and this condition may or may not be accompanied by symptoms such as anorexia, dizziness, bone pain, proximal muscular weakness, and waddling gait. While reduction of serum phosphorus below 1.0 mg/dL suggests severe hypophosphatemia, the condition may not be fully diagnostic. For example, severe hypophosphatemia and severe total body deficiencies of phosphorus may occur in patients with temporary poor dietary intake of phosphorus-containing foods, or in patients consuming phosphate-binding antacids, or with patients presenting early-stage diabetic ketoacidosis.

Hypophosphatemia manifests itself in many different syndromes that may occur simultaneously. In severe hypophosphatemia (which may be aggravated by administration of nutrients to alcoholics or with therapy for diabetic ketoacidosis), elevations in serum creatine phosphokinase (CPK) suggest that the rhabdomyolysis may be superimposed on myopathy. This sequence of events also occurs in experimental phosphate depletion in animals. Severe congestive cardiomyopathy has been noted with chronic hypophosphatemia, and restoration of the phosphorus deficit leads to prompt reversal of the abnormalities. The bone pain and waddling gait seen in hypophosphatemia patients are attributed to the osteomalacia (i.e., failure of normal bone mineralization brought about by the kidney's failure to supply the active form of vitamin D) that develops as a result of phosphate depletion; and the muscular weakness may be due either to direct effects of hypophosphatemia on nerves and muscle or to the effects of hyperparathyroidism that may have a role in the etiology of the hypophosphatemia. Defective growth in children may also be due to phosphate depletion. Hypophosphatemia also results in decreased levels of 2,3-diphosphoglyceric acid and adenosine triphosphate in red blood cells that in turn alter the dissociation of oxyhemoglobin so that less oxygen is delivered in the periphery which mechanism my explain the central nervous system dysfunction seen in hypophosphatemia patients.

Negative phosphorus balance is rarely caused by inadequate phosphorus adsorption I n the intestine. Maintenance of normal phosphorus balance is dependent upon efficiency of renal excretion of conservation. In severe renal failure, hyperphosphatemia results from inadequate renal phosphorus clearance; heritable or acquired renal tubular defects may lead to hypophosphatemia due to inadequate renal conservation of phosphorus.

Hyperphosphatemias defined in adults as an elevation of serum phosphorus above 5 mg/dL. Unfortunately, the condition produces no direct symptoms. However, with maintenance of high phosphorus levels for long periods of time, the driving force for mineralization is increased, and calcium phosphate may be deposited in abnormal sites. Severe hyperphosphatemia is normally associated with extensive cellular or tissue damage. The combination of an increased release of phosphate from damaged muscle tissue and an impaired ability to excrete phosphorous secondary to renal failure (the most common cause of hyperphosphatemia) causes moderate to severe hyperphosphatemia.

Hyperphosphatemia with levels of to 40 mg/dL and above, has occurred secondary to increased absorption from the intestines following administration of excess phosphate salts orally or from the colon as a result of enemas containing phosphate salts. Overmedication with vitamin D, and its production by granulomatous tissue in diseases such as sarcoidosis and tuberculosis may cause hyperphosphatemia. Lactic acidosis is especially important as a cause of hyperphosphatemia. Other causes of hyperphosphatemia may be found in pathologies involving decresed renal excretion such as in the case of renal insufficiency, hypoparathyroidism, hyperostasis, adrenal insufficiency, and infantile hypooshosphatasis; involving intestinal absorption such as in vitamin D ingestion, and granulomatous diseases producing vitamin D (as, for example, tuberculosis); involving internal redistribution of phosphorus such as lactic acidosis, reduced insulin level, acute respiratory acidosis, and lactic acid infusion; involving cellular release of phosphorus such as rhabdomyolysis, tumor lysis, and acute hemolysis; involving parenteral administration of phospholipids infusions or intravenous phosphate salts; and involving spurious hyperphosphatemia such as in thrombocytosis and hyperlipidemia.

Hyperphosphatemia is potentially dangerous because it may lead to hypercalcemia resulting in metastatic calcifications in extraordinary sites such as muscle tissue, or within the cardiovascular system. Known causes of hyperphosphatemia that may lead to hypercalcemia include hypothermia, massive hepatic failure, and hematologic malignancies either because of high cell turnover as part of the malignancy or because of cell destruction when chemotherapy is instituted.

The threat of calcification occurrence from the widespread deposition of calcium disappears after restoration of phosphate levels to normal ranges. At the present time, treatment of hyperphosphatemia involves the use of aluminum-based antacids that bind phosphorus in the lumen of the gastrointestinal tract and prevent its absorption. Although long-term use of aluminum-based antacids should be avoided because they may result in aluminum toxicity, short-term use is acceptable.

The present invention is based upon the new and unexpected finding of a new basis upon which to diagnose and treat hypophosphatemia conditions in mammals, and a new and unexpected treatment for mammalian hyperphosphatemia.

Accordingly, it is one aspect of the present invention to describe a method of diagnosing a hypophosphatemic disorder in a mammal.

It is another aspect of the present invention to describe a biologically-active biopolymer for the treatment of hypophosphatemic disorders in a mammal.

Yet another aspect of the present invention is to describe a biologically-active biopolymer for the treatment of hyperphosphatemic disorders in a mammal.

These and other aspects of the present invention will become more readily apparent to the reader in the following discussion and description, both provided for purposes of disclosure and clarity and not as a limitation to the scope of the invention being described, taken with the accompanying drawings.

DETAILED DESCRIPTION OF THE INVENTION

Phosphate is a nutrient essential for many biological processes including skeletal mineralization and energy metabolism. The homeostasis of the plasma phosphate level is essential for these processes. The reabsorption of phosphate in the kidney is a major determinant of the plasma phosphate level in humans. This phosphate transport occurs primarily via the NaPi2 class of cotransporters in the proximal renal tubule. One such acquired disorder of phosphate homeostasis is oncogenic osteomalacia which is also referred to as tumor-induced osteomalacia (TIO). TIO is marked by renal phosphate-wasting disorder resulting in low serum phosphorus concentration and osteomalacia. Removal of the tumor normalizes phosphate metabolism. Additionally recent studies have identified that phosphatonin to be identical to fibroblast growth factor 23 (FGF-23) (see Proc. Natl. Acad. Sci., 2001, vol: 98, 6500-6505). FGF-23 is the recently identified member of the FGF family. While previous studies suggest that overproduction of FGF23 causes TIO, there is speculation that mutation in FGF-23 gene results in autosomal dominant hypophosphatemic rickets (ADHR) (see Nat. Genet. 2000, 26:345-348). ADHR is yet another phosphate wasting disorder resulting in low serum phosphorus concentration, rickets and osteomalacia. Previous studies show no evidence that recombinant FGF-23 can inhibit phosphate uptake in renal proximal epithelial cells. The present invention differs from the existing literature that the fibroblast growth factor 20 (FGF20) inhibited serum phosphate levels in the tested animal models.

The present invention describes the novel use of FGF20 and other fibroblast growth factors in reduction of serum phosphates. Furthermore, the present invention also indicates the possible mechanism by which the fibroblast growth factors may be modulating the phosphate transport. This may have important implications in various phosphate wasting disorders as described above.

Methods that may be employed to identify relevant biological macromolecules include any procedures that detect differential expression of nucleic acids encoding proteins and polypeptides associated with the disorder, as well as procedures that detect the respective proteins and polypeptides themselves.

Proper serum phosphate concentrations are maintained by a complex and poorly understood process. Identification of genes responsible for inherited disorders involving disturbances in phosphate homeostasis may provide insight into the pathways that regulate phosphate balance.

The present invention identifies a set of proteins and polypeptides, including naturally occurring polypeptides, precursor forms or proproteins, or mature forms of the polypeptides or proteins, which are implicated as targets for therapeutic agents in the treatment of various diseases, pathologies, abnormal states and conditions. A target may be employed in any of a variety of screening methodologies in order to identify candidate therapeutic agents which interact with the target and in so doing exert a desired or favorable effect. The candidate therapeutic agent is identified by screening a large collection of substances or compounds in an important embodiment of the invention. Such a collection may comprise a combinatorial library of substances or compounds in which, in at least one subset of substances or compounds, the individual members are related to each other by simple structural variations based on a particular canonical or basic chemical structure. The variations may include, by way of nonlimiting example, changes in length or identity of a basic framework of bonded atoms; changes in number, composition and disposition of ringed structures, bridge structures, alicyclic rings, and aromatic rings; and changes in pendent or substituents atoms or groups that are bonded at particular positions to the basic framework of bonded atoms or to the ringed structures, the bridge structures, the alicyclic structures, or the aromatic structures.

A polypeptide or protein described herein, and that serves as a target in the screening procedure, includes the product of a naturally occurring polypeptide or precursor form or proprotein. The naturally occurring polypeptide, precursor or proprotein includes, e.g., the full-length gene product, encoded by the corresponding gene. The naturally occurring polypeptide also includes the polypeptide, precursor or proprotein encoded by an open reading frame described herein. A "mature" form of a polypeptide or protein arises as a result of one or more naturally occurring processing steps as they may occur within the cell, including a host cell. The processing steps occur as the gene product arises, e.g., via cleavage of the amino-terminal methionine residue encoded by the initiation codon of an open reading frame, or the proteolytic cleavage of a signal peptide or leader sequence. Thus, a mature form arising from a precursor polypeptide or protein that has residues 1 to N, where residue 1 is the N-terminal methionine, would have residues 2 through N remaining. Alternatively, a mature form arising from a precursor polypeptide or protein having residues 1 to N, in which an amino-terminal signal sequence from residue 1 to residue M is cleaved, includes the residues from residue M+1 to residue N remaining. A "mature" form of a polypeptide or protein may also arise from non-proteolytic post-translational modification. Such non-proteolytic processes include, e.g., glycosylation, myristylation or phosphorylation. In general, a mature polypeptide or protein may result from the operation of only one of these processes, or the combination of any of them.

As used herein, "antibodies" encompass antibodies and antibody fragments, such as Fab, $(Fab)_2$ or single chain FV constructs, that bind immunospecifically to any of the proteins of the invention. Also encompassed within the invention are peptides and polypeptides comprising sequences having high binding affinity for any of the proteins of the invention, including such peptides and polypeptides that are fused to any carrier particle (or biologically expressed on the surface of a carrier) such as a bacteriophage particle.

Probes based on the human FGF nucleotide sequences can be used to detect transcripts or genomic sequences encoding the same or homologous proteins. In various embodiments, the probe further comprises a label group attached thereto, e.g. the label group can be a radioisotope, a fluorescent compound, a bioluminescent compound, a chemiluminescent compound, a metal chelate, an enzyme, or an enzyme co-factor. Such probes can be used as a part of a diagnostic test kit for identifying cells or tissues which mis-express an FGF protein, such as by measuring a level of an FGF encoding nucleic acid in a sample of cells from a subject e.g., detecting FGF MRNA levels or determining whether a genomic FGF gene has been mutated or deleted.

In one embodiment, the invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an FGF protein, mRNA, or genomic DNA in the preadministration sample; (iii) obtaining one or more post-administration samples from the subject; (iv) detecting the level of expression or activity of the FGF protein, mRNA, or genomic DNA in the post-administration samples; (v) comparing the level of expression or activity of the FGF protein, MRNA, or genomic DNA in the pre-administration sample with the FGF protein, mRNA, or genomic DNA in the post administration sample or samples; and (vi) altering the administration of the agent to the subject accordingly. For example, increased administration of the agent may be desirable to increase the expression or activity of FGF to higher levels than detected, i.e., to increase the effectiveness of the agent. Alternatively, decreased administration of the agent may be desirable to decrease expression or activity of FGF to lower levels than detected, i.e., to decrease the effectiveness of the agent.

Another aspect of the invention pertains to methods of modulating FGF expression or activity for therapeutic purposes. The modulatory method of the invention involves contacting a cell with an agent that modulates one or more of the activities of FGF protein activity associated with the cell. An agent that modulates FGF protein activity can be an agent as described herein, such as a nucleic acid or a protein, a naturally-occurring cognate ligand of an FGF protein, a peptide, an FGF peptidomimetic, or other small molecule. In one embodiment, the agent stimulates one or more FGF protein activity. Examples of such stimulatory agents include active FGF protein and a nucleic acid molecule encoding FGF that has been introduced into the cell. In another embodiment, the agent inhibits one or more FGF protein activity. Examples of such inhibitory agents include antisense FGF nucleic acid molecules and anti-FGF antibodies. These modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of an FGF protein or nucleic acid molecule. In one embodiment, the method involves administering an agent (e.g., an agent identified by a screening assay described herein), or combination of agents that modulates (e.g., up-regulates or down-regulates) FGF expression or activity. In another embodiment, the method involves administering an FGF protein or nucleic acid molecule as therapy to compensate for reduced or aberrant FGF expression or activity.

The present invention described herein, i.e., methods for diagnosing and treating conditions that alter phosphate transport in mammals is the result of finding and identifying a biologically-active biopolymer that reduces serum phosphate levels in mammals. More specifically, a protein molecule has been identified that shows new and unexpected activity in reducing serum phosphate. This finding suggests that the biopolymer may be useful in the treatment of those disease states wherein serum phosphate levels are high, and it also suggested suggesting that antagonism of this protein, or its pathway, may be useful in the treatment of serum hypophosphatemia conditions under various disease pathologies in which low phosphate levels are found. In very significant embodiments of the present invention, the biological macromolecules implicated in these pathologies and conditions are proteins and polypeptides, and in such cases the present invention is related as well to the nucleic acids that encode them.

The biologically active biopolymer that has been unexpectedly found to reduce serum phosphate levels in mammals according to the present invention is a member of the fibroblast growth factor family, specifically FGF 20 and their variants as detailed in U.S. Ser. Nos. 10/174,394 and 10/435,087. The biopolymer according to the present invention may, for use in the reduction of serum phosphate levels be isolated and purified from natural sources, or may be in the form of recombinant FGF 20.

Other active polypeptides that are discussed with supportive data in the current disclosure, that could alter phosphate transport and related conditions discussed above, are FGF 9 and FGF 10.

The biologically active polypeptides of the invention disclosed herein are human FGF 20, FGF 9 and FGF 10 that are known in the public domain. Physical clones have been derived by laboratory cloning of cDNA fragments, by in silico prediction of the sequence.

FGF 20: Swiss-Prot Accession No: Q9NP95 and variants of FGF 20 (U.S. Ser. Nos. 10/174,394 and 10/435,087)
FGF 9: Swiss-Prot Accession No: P31371
FGF 10: Swiss-Prot Accession No: O15520

EXAMPLE 1

To evaluate the role of FGF20 in reduction of phosphate levels, two different animal models (rat and rhesus monkeys) were tested for serum phosphates following treatment with FGF20. Recombinant human FGF20 and the serum phosphate levels were measured. General protocols for the rat and Rhesus monkey models are outlined in the following Tables 1 (for the rat) and 2 (for the Rhesus monkey) below:

TABLE 1

Group Designation and Dosage Levels

| Group No. | Dose Level (mg/kg) | Dose Conc. (mg/mL) | Main Study segment* Dosed through SD 7 | | Dosed through SD 14 | | Recovery Segment** Dosed through SD 14; recovery through SD 28 | |
|---|---|---|---|---|---|---|---|---|
| | | | Males | Females | Males | Females | Males | Females |
| 1 | 0 | 0 | 10 | 10 | 10 | 10 | 5 | 5 |
| 2 | 0.05 | 0.01 | 10 | 10 | 10 | 10 | 5 | 5 |
| 3 | 5 | 1 | 10 | 10 | 10 | 10 | 5 | 5 |
| 4 | 50 | 10 | 10 | 10 | 10 | 10 | 5 | 5 |

The first 10 sex/group are main study animals necropsied on SD 8; the next 10/sex/group are main study animals necropsied on SD 15, the next 5/sex/group are recovery animals necropised on SD 29. Dose volume are 5 ml/kg.
*All main segment animals were treated for 7 or 14 days with either CG53135-05 or vehicle alone.
**All recovery segment animals were treated for 14 days followed by a recovery period for 14 days.

TABLE 2

Group Designation and Dosage Levels

| Group | Treatment | Dose Level (mg/kg) | Dose Concentration (mg/mL) | Study Animals* | |
|---|---|---|---|---|---|
| | | | | Males | Females |
| 1 | Vehicle Control | 0 | 0 | 2 | 2 |
| 2 | CG53135-05 | 1 | 1 | 2 | 2 |
| 3 | CG53135-05 | 10 | 10 | 2 | 2 |

*All treatment animals were treated for 7 days with either CG53135-05 or vehicle alone followed by a recovery period for 7 days. Assessment of antibodies continued for 28 days after dosing period ended.

Both animal groups were dosed via a slow bolus intravenous injection in the tail vein, once daily for 14 days. The first day of dosing was designated as study day ("SD") 1. Animals were dosed through SD 14.

Clinical Pathology: Table 3 shows the schedule of the clinical pathology assessed in both the animal models.

TABLE 3

Chemistry, Hematology, Coagulation and Urinalysis

| Procedure | Time Point | Sample (Blood or Urine) Volume | Collection Device[c] |
|---|---|---|---|
| Chemistry[a] | Prior to scheduled necropsies | 1 mL + 15% (Blood) | Serum separator tubes |
| Hematology[a] | Prior to scheduled necropsies | 0.5 mL + 15% (Blood) | Tubes containing potassium EDTA |
| Coagulation[a] | Prior to scheduled necropsies | 1.8 mL ± 15% (Blood) | Tubes containing sodium Citrate |
| Urinalysis[b] | Prior to scheduled necropsies | At the end of the collection period, measure and record Urine volume | Polycarbonate metabolic cages |

Figure 1:
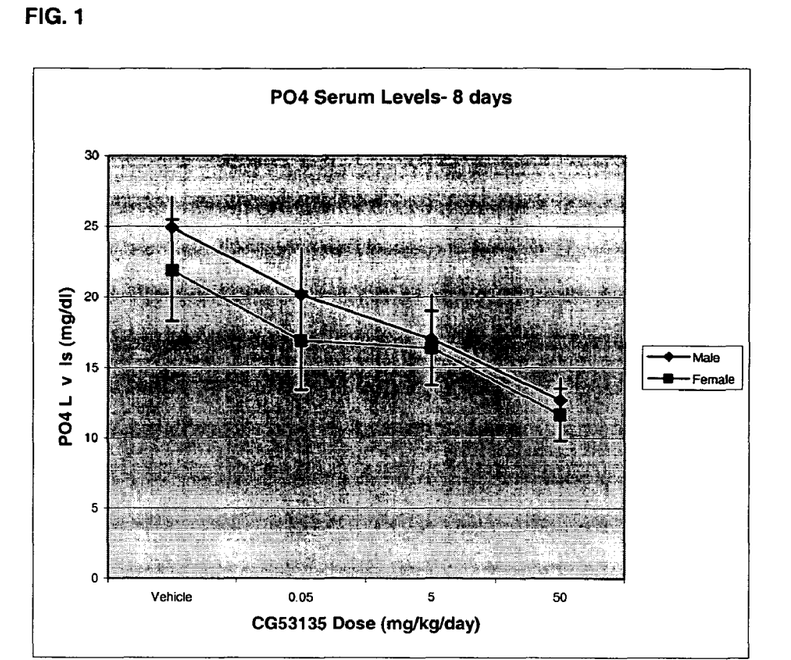
FIG. 1 depicts a graphical representation of serum phosphate levels following treatment of a first mammalian model utilizing the biopolymer FGF-20 (CG53135-05) according to the present invention.
Figure 2:
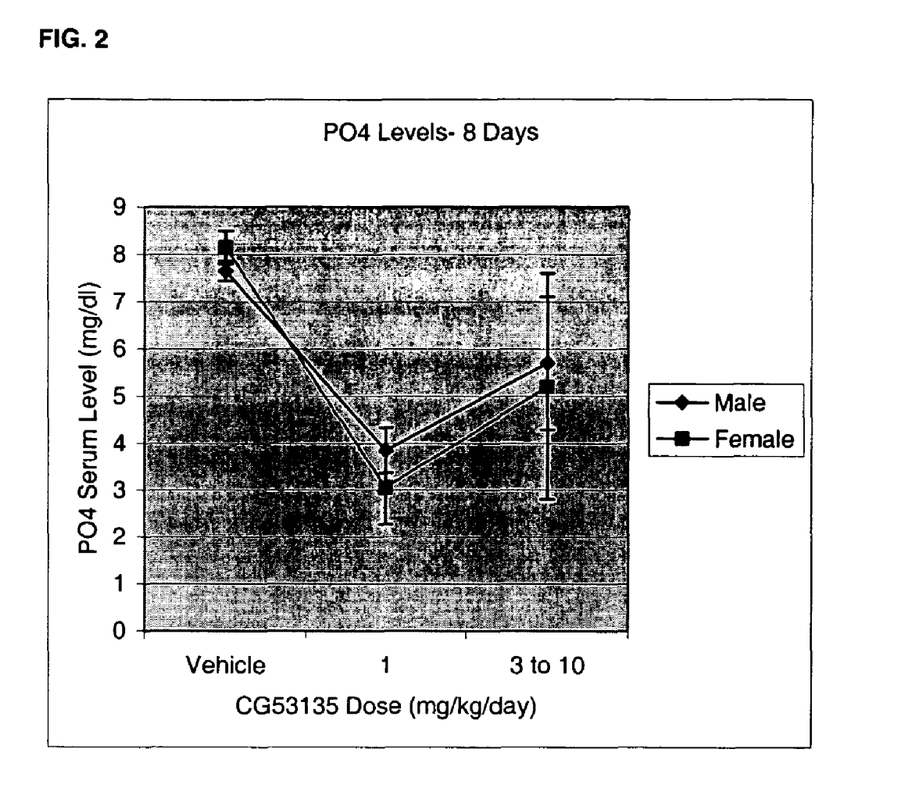
FIG. 2 depicts a graphical representation of serum phosphate levels following treatment of a second mammalian model utilizing the biopolymer FGF 20 (CG53135-05) according to the present invention.

Results: Statistically significant reductions of serum phosphate levels were observed in both the rat and Rhesus monkey models in a dose-dependent manner (FIG. 1 and FIG. 2), suggesting that human FGF20 and other members of the fibroblast growth factor family that activate the same receptor may be useful for the treatment of hyperphosphatemia.

EXAMPLE 2

Background

FGF family members transduce signals intracellularly via high affinity interactions with cell surface immunoglobulin (Ig) domain-containing tyrosine kinase FGF receptors (FGFRs). Four distinct human genes encode FGFRs (see Endocr. Relat. Cancer 2000, 7:165-97; see Front. Biosci. 1999, 4:D165-77; see Cell Tissue Res. 1999, 296:33-43). A related fifth human sequence lacking a kinase domain has recently been identified and named FGFR-5 (see Biochim Biophys Acta 2001, 1518:152-6). These receptors can each bind several different members of this family (see Biochim Biophys Acta 2001, 1518:152-6; see J Biol Chem 1996, 271:15292-7). FGFs also bind, albeit with low affinity, to heparin sulfate proteoglycans (HSPGs) present on most cell surfaces and extracellular matrices (ECM). Interactions between FGFs and HSPGs serve to stabilize FGF/FGFR interactions and to sequester FGF and protect it from degradation (see Endocr. Relat. Cancer 2000, 7:165-97; see Int. Rev. Cytol. 1999,185:45-106). Dimerization of FGF receptor monomers upon ligand binding is reported to be a requisite for activation of the kinase domains, leading to receptor trans-phosphorylation. FGF receptor-1 (FGFR-1), which shows the broadest expression pattern of the four FGF receptors, contains at least seven tyrosine phosphorylation sites. A number of signal transduction molecules are affected by binding with different affinities to these phosphorylation sites.

FGFR-1, FGFR-2 and FGFR-3 each recognize FGF-1, FGF-2, FGF-4 and FGF-8. In addition, FGFR-1 & FGFR-2 bind FGF-3, FGF-5, FGF-6, FGF-10 and FGF-17 (see Endocr. Relat. Cancer 2000, 7:165-97). Binding of various FGF ligands varies with each receptor splice form, thus allowing a wide repertoire of FGF-mediated signaling events through a limited number of receptor coding genes. Tissue-specific alternate splicing permits cells expressing a single FGFR gene to significantly diversify their biological response by generating distinct receptor isoforms that may exhibit different ligand specificity and function. FGFR-4, binds FGF-1, FGF-2, FGF-4, FGF-6, FGF-8 and FGF-9 but not FGF-3, FGF-5 or FGF-7. FGF-7, or keratinocyte growth factor-1 (KGF-1) is only recognized by FGFR-2, whereas FGF-9 binds to FGFR-2, FGFR-3 and FGFR-4. Receptor specificity of FGFs-11 to -19 is not well understood (see Endocr. Relat. Cancer 2000, 7:165-97; see J. Biol. Chem. 1996, 271:15292-7).

Immunohistochemistry studies (see J. Histochem. Cytochem. 1997, 45:1005-19) in normal human adult tissues from the major organ systems indicated that FGFR-1, FGFR-2 and FGFR-3 are widely expressed, suggesting an important functional role in tissue homeostasis. Protein expression patterns for tissue-specific isoforms have not yet been determined. FGFR-4 has a more limited expression pattern being notably absent from lung, oviduct, placenta, testis, prostate, thyroid, parathyroid, and sympathetic ganglia, tissues where all three other receptors are predominantly expressed (see J. Histochem. Cytochem. 1997, 45:1005-19).

To determine the receptor binding specificity of FGF20, the effect of soluble FGFRs on the induction of DNA synthesis in NIH 3T3 cells by recombinant CG53135-05 produced in *E. coli* was examined.

Materials and Methods

Protein Purification from *Escherichia coli* For production in *E. coli*, plasmid pETMY-hFGF20X was transformed into the *E. coli* expression host BL21 (Novagen, Madison, Wis.) and the induction of protein CG53135-05 expression was carried out according to the manufacturer's instructions. pETMYhFGF20X/BL21 *E. coli* bacteria were grown in LB medium at 37□C. At an OD of 0.6, *bacteriophage lambda* (CE6) was added to a final multiplicity of infection of 5. The infected culture was further incubated at 27° C. for 3 hours. After induction, total cells were harvested, and proteins were analyzed by Western blotting using anti-HisGly antibody (Invitrogen). Cells were harvested by low-speed centrifugation (5000 rpm in a GS-3 rotor for 15 minutes at 4° C.), suspended in phosphate-buffered saline (PBS) containing 0.5M NaCl and 1M arginine, and disrupted with two passes through a microfluidizer. Cell debris was removed by low-speed centrifugation and the soluble protein fraction (supernatant) was clarified by filtration through a 0.2 micron low-protein binding membrane. The protein sample was then loaded onto a metal chelation column (pre-charged with nickel sulfate). The nickel column was washed with PBS/ 0.5M NaCl+1M L-arginine and bound proteins were eluted with a linear gradient of imidazole (0-0.5 M). Fractions containing CG53135-05 (100-150 mM imidazole) were pooled and dialyzed against 1×106 volumes of PBS pH 8.0 containing 1M L-arginine. The protein sample was stored at −80° C.

Receptor Specificity NIH 3T3 cells were cultured in 96-well plates to approximately 100% confluence, washed and fed with DMEM without supplements (Life Technologies), and incubated for 24 h. Recombinant CG53135-01 or control protein was then added to the cells for 18 h. Control proteins used were aFGF (positive control) and platelet derived growth factor-BB (PDGFBB) (negative control). To analyze the effect of soluble FGFRs on CG53135-05 activity, recombinant CG53135-05, aFGF, or PDGF-BB (final concentrations of 10, 5 and 3 ng/mL, respectively), were mixed with soluble receptors (final concentrations of 0.2, 1 and 5 ug/mL), and incubated for 30 min at 37° C. prior to addition to serum-starved NIH 3T3 cells. Factor concentrations represent the amount of ligand needed to generate a half maximal BrdU response in NIH 3T3 cells. Soluble FGFRs were Fc chimeras of the following receptor forms (FGFR1β(IIIc); FGFR2β(IIIb); FGFR2α(IIIb); FGFR2α (IIIc); FGFR3α(IIIc); FGFR4) and were obtained from R&D Systems (Minneapolis, Minn.). The BrdU assay was performed according to the manufacturer's specifications (Roche Molecular Biochemicals, Indianapolis, Ind.) using a 4 h BrdU incorporation time.

Results and Conclusions

Figure 3:
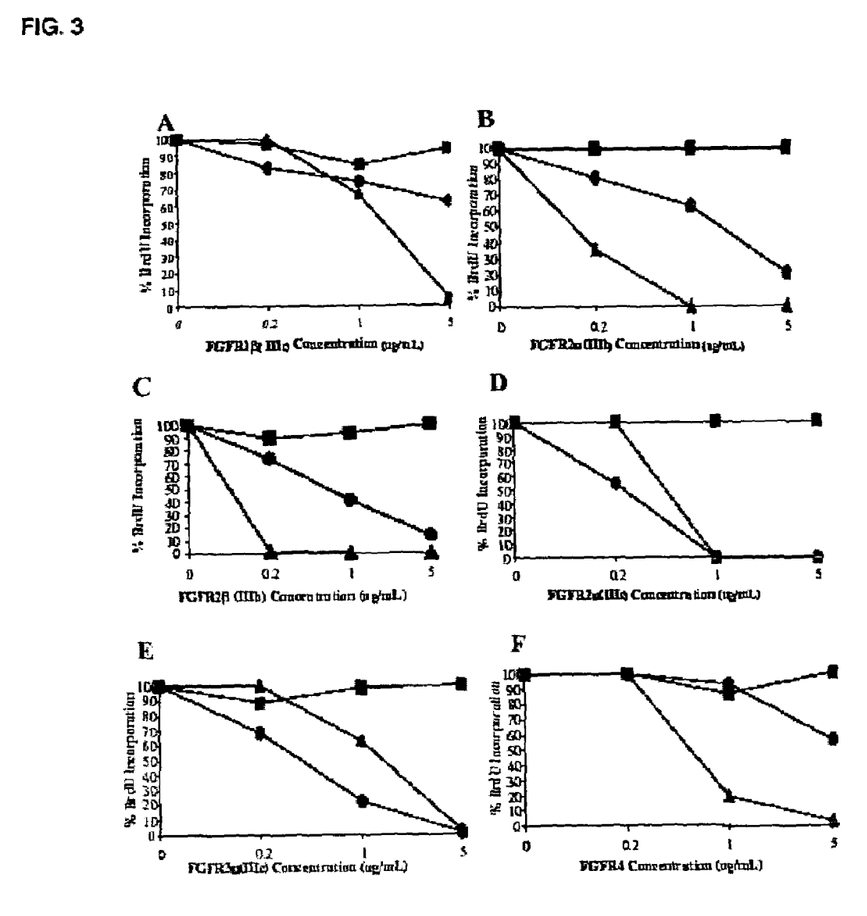
FIG. 3. Effect of soluble FGF receptors on the induction of DNA synthesis in NIH 3T3 cells by recombinant FGF 20. NIH 3T3 cells were serum-starved, incubated with the indicated factor (square=platelet derived growth factor; triangle=FGF 1; circle=FGF 20) either alone or together with the indicated soluble FGFR. DNA synthesis in response to FGF 20 was measured in a BrdU incorporation assay. Data points represent the average obtained from triplicate wells, and are represented as the percent BrdU incorporation relative to cells receiving factor alone.

To determine the receptor binding specificity of CG53135-05, we examined the effect of soluble FGFRs on the induction of DNA synthesis in NIH 3T3 cells by recombinant CG53135-05 produced in *E. coli*. Soluble receptors for FGFR1β(IIIc), FGFR2β(IIIb), FGFR2β(IIIb), FGFR2α (IIIc), FGFR3α(IIIc), and FGFR4 were utilized. We found that soluble forms of each of these FGFRs were able to specifically inhibit the biological activity of CG53135-05 (FIG. 3).

Complete or nearly complete inhibition was obtained with soluble FGFR2α(IIIb), FGFR2β(IIIb), FGFR2α(IIIc), and FGFR3α(IIIc), whereas partial inhibition was achieved with soluble FGFR1β(IIIc) and FGFR4. None of the soluble receptor reagents interfered with the induction of DNA synthesis by PDGF-BB (FIG. 3), thereby demonstrating their specificity. The integrity of each soluble receptor reagent was demonstrated by showing their ability to inhibit the induction of DNA synthesis by aFGF, a factor known to interact with all of the FGFR's under analysis (FIG. 3).

EXAMPLE 3

Figure 4:
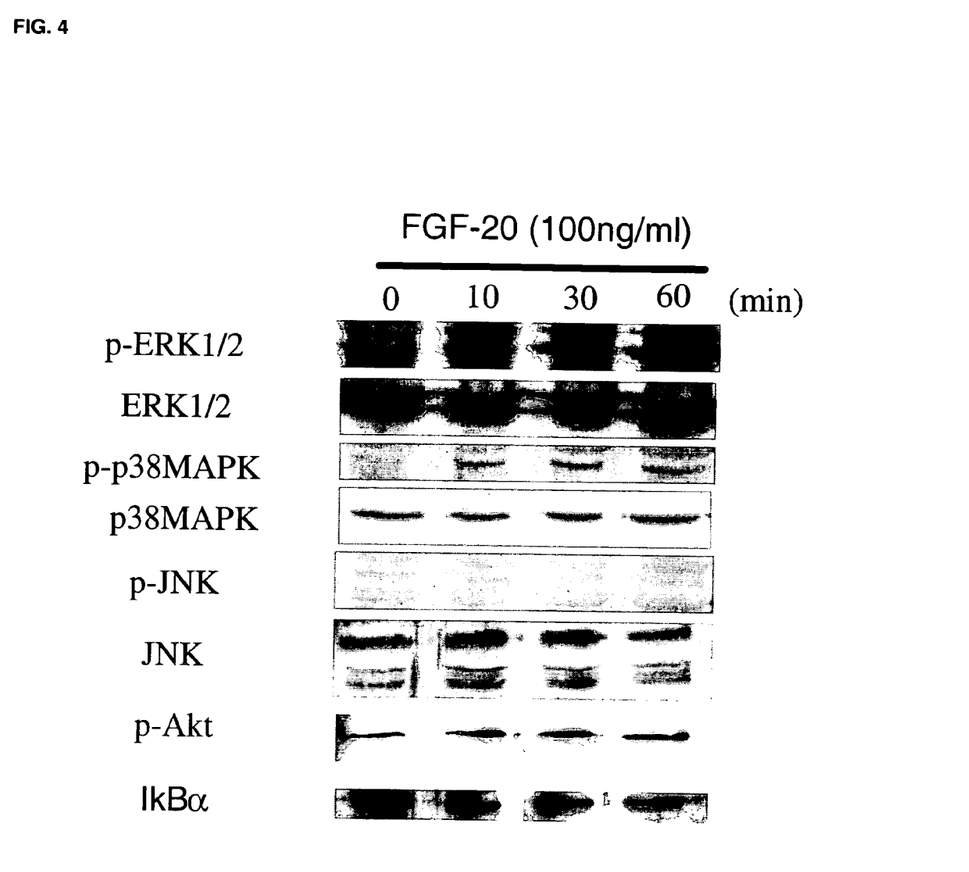
FIG. 4 depicts effect of FGF20 (CG53135) in stimulation of kinases in Caco2 cells. Expression of signal transducing kinases was analyzed after incubation of Caco2 cells with FGF-20 (100 ng/ml) for different time points (10, 30, 60 mins).
Figure 5:
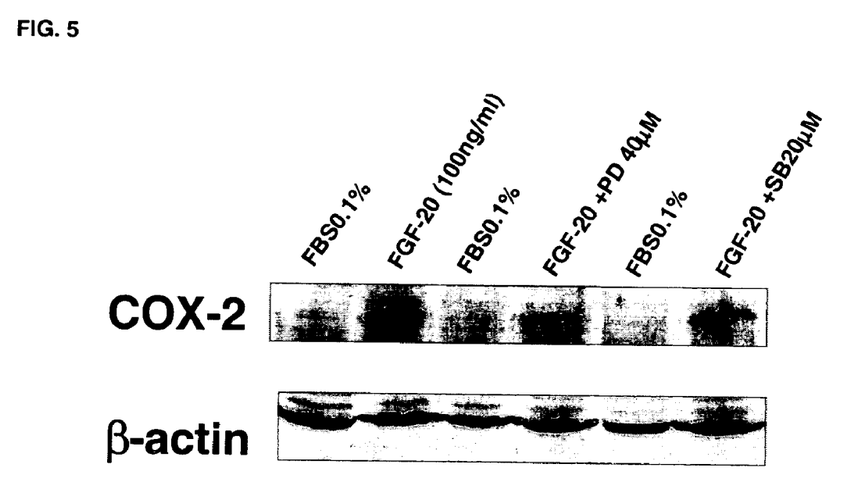
FIG. 5 depicts effect of kinase inhibitors in the expression of COX-2 gene in Caco2 cells. Caco2 cells were incubated with FGF-20 (100 ng/ml) in the presence of 40 µM of PD098059 and 20 µM of SB203580 and COX-2 expression was analyzed.
Figure 6:
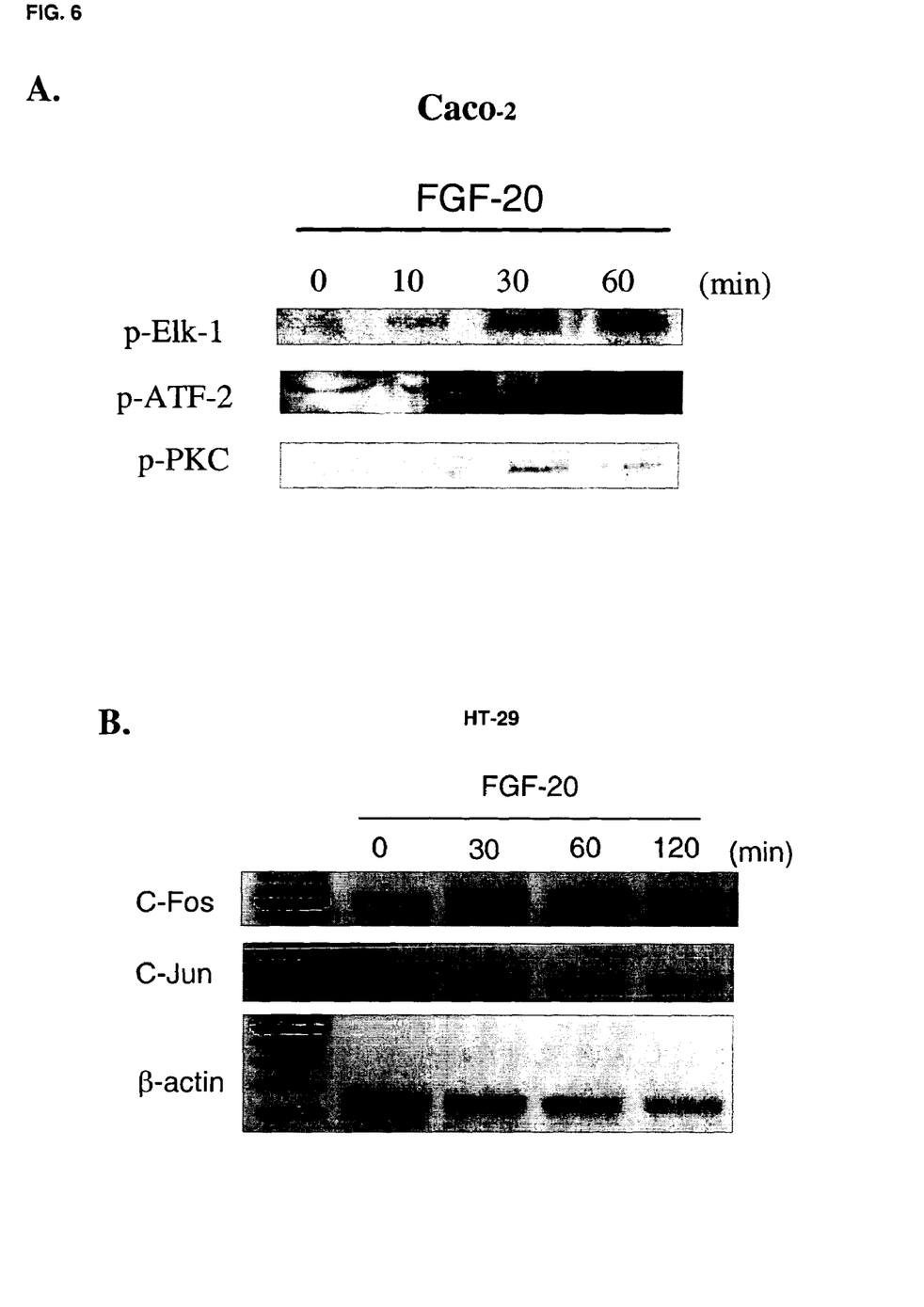
FIG. 6 depicts Effect of FGF-20 on expression of kinases in intestinal epithelial cells. Caco2 cells were incubated with FGF-20 (100 ng/ml) for 10, 30, 60 minutes and expression of p-Elk-1, p-ATF-2 and p-PKC was analyzed. Similarly, HT-29 cells were incubated with FGF-20 (100 ng/ml) for 10, 30, 60 minutes and expression of C-Fos and C-Jun was analyzed.

MAPK-dependent mechanism may be involved in the regulation of phosphate uptake by FGF signaling. To test this hypothesis, various kinases were tested for their expression in the presence of 100 ng/ml of FGF-20, in Caco2 cells. The results indicated that phosphorylated MAPK (p-p38MAPK) was induced in the presence of FGF-20, while no other kinase tested, showed any significant induction (FIG. 4). In addition, FIG. 5 demonstrates that inhibitors of Erk and MAPK decreased COX-2 expression in the presence of FGF-20, in Caco2 cells. Also FIG. 6 shows increased expression of phosphorylated Elk-1, ATF-2 and minimal induction of phosphorylated Protein Kinase C in Caco-2 cells in the presence of FGF-20. In HT-29 cells, C-Fos and C-Jun were induced, when cultured with FGF-20 (FIG. 6).

Figure 7:
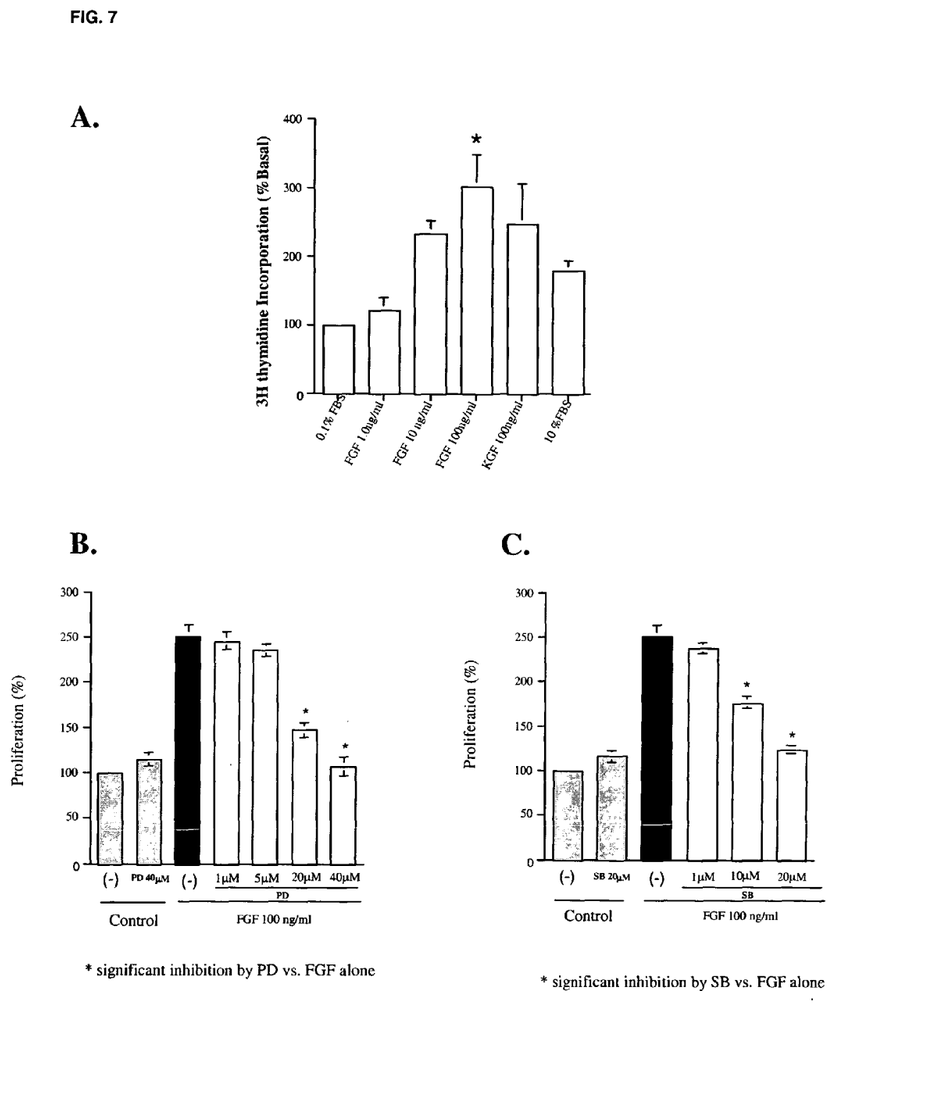
FIG. 7 depicts effect of kinase inhibitors in the proliferation of Caco2 cells. Caco2 cells were incubated with FGF-20 (100 ng/ml) in the presence of various concentrations (1, 5, 20 and 40 µM) of PD098059, inhibitor of MEK which is upstream of ERK or various concentrations (1, 10, 20 µM) of SB203580, inhibitor of p38 MAPK inhibitor.

In addition to the above results, MEK inhibitor PD098059 (1, 5, 20, and 40μM CALBIOCHEM, CA), and p38 MAPK inhibitor SB203580 (1,10,20 μM CALBIOCHEM, CA) were added to the Caco2 cell cultures 1 hr before FGF-20 treatment. Cellular proliferation was tested by standard 3H thymidine incorporation assay known in the art. Proliferation results in Caco-2 cells show that there is a decrease in cellular proliferation when the kinases are inhibited (FIG. 7).

From the above data, it appears that phosphate wasting may occur in response to a variety of factors including FGF receptor signaling.

EXAMPLE 4

To detect the MAPK pathway in OK cells, OK cells are cultured and the cell lysates run in SDS-polyacrylamide gel electrophoresis under reducing conditions and transferred to nitrocellulose membranes. Phosphorylated ERK or p38-MAPK is detected by Western Blotting analysis using rabbit antibodies against phospho-ERK or phospho-p38 MAPK.

Measurement of phosphate transport is performed in cultured renal proximal tubular epithelial cell line using opossum kidney (OK) cells, in the presence of FGF-20 (CG53135-05). Briefly, OK cells are grown at 37° C. in Dulbecco's modified Eagle's medium with 10% fetal calf serum and seeded in multi-well dishes (6, 24, 96 well dishes). The phosphate uptake in OK cells is determined according to the method described by Hafdi et al (Biochem. J. 1996, 320:615-621).

To further delineate the MAPK-dependent mechanism, OK cells are cultured with FGF-20 and protein kinase inhibitors of FGF receptors (Ex: MAPK, Erk) and phosphate transport is measured.

EXAMPLE 6

Figure 8:
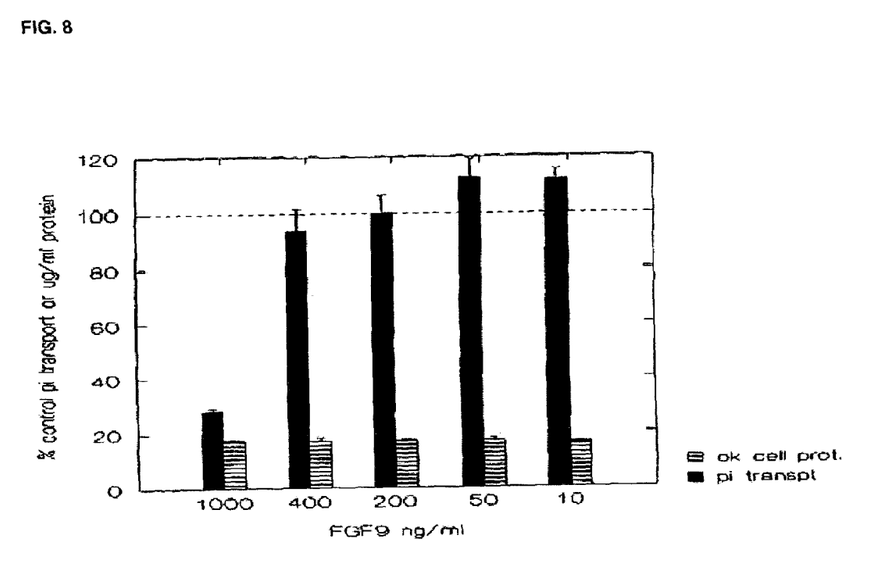
FIG. 8 depicts effect of FGF9 protein in phosphate transport. OK cells were treated with various concentrations of FGF9 protein and phosphate uptake was measured as noted in Example 6.
Figure 9:
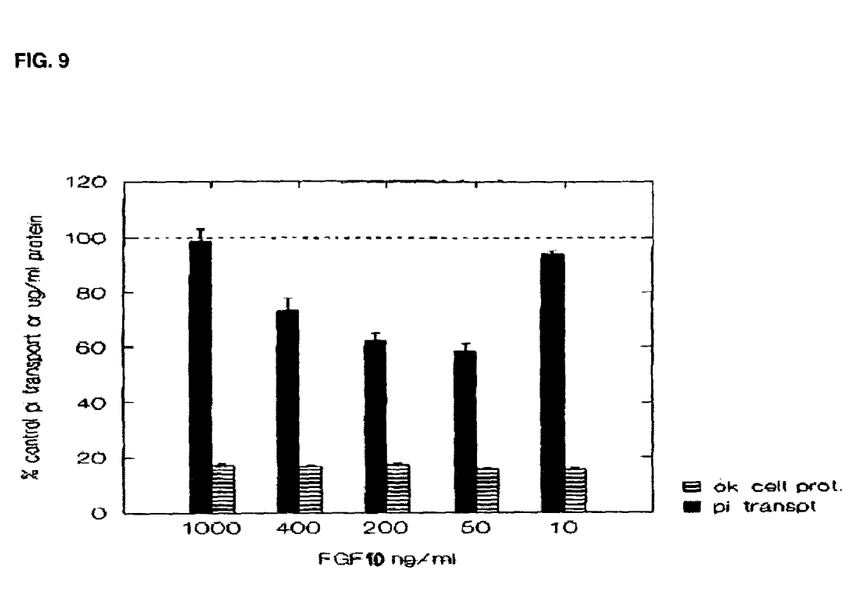
FIG. 9 depicts effect of FGF10 protein in phosphate transport. OK cells were treated with various concentrations of FGF10 protein and phosphate uptake was measured as noted in Example 6.

Role of FGF9 and FGF10 in phosphate uptake was measured by the method described in Biochem. J. 1996, 320:615-621. The results demonstrate that FGF9 inhibits phosphate transport at 1000 ng/ml in the OK cells (FIG. 8) while FGF10 protein was more efficient in inhibiting the phosphate transport at 50 ng/ml (FIG. 9). These results also indicate that FGF10 effect may be mediated through FGFR2b receptor.

Thus these fibroblast growth factors can be used as a therapeutic for hyperphosphatemia and the antibodies to these growth factors can be used in the treatment or prevention of phosphate wasting seen in hypophosphatemia.

Thus, I have illustrated and described the preferred embodiment of our invention, it is to be understood that this invention is capable of variation and modification, and I therefore do not wish to be limited to the precise terms set forth, but desire to avail myself of such changes and alterations which may be made for adapting the invention to various usages and conditions. Such alterations and changes may include, for different compositions for the administration of the polypeptides according to the present invention to a mammal; different amounts of the polypeptide; different times and means of administration; different materials contained in the administration dose including, for example combinations of different peptides, or combinations of peptides with different biologically active compounds. Such changes and alterations also are intended to include modifications in the amino acid sequence of the specific polypeptides described herein in which such changes alter the sequence in a manner as not to change the functionality of the polypeptide, but as to change solubility of the peptide in the composition to be administered to the mammal, absorption of the peptide by the body, protection of the polypeptide for either shelf life or within the body until such time as the biological action of the peptide is able to bring about the desired effect, and such similar modifications. Accordingly, such changes and alterations are properly intended to be within the full range of equivalents, and therefore within the purview of the following claims. Having thus described my invention and the manner and process of making and using it in such full, clear, concise and exact terms so as to enable any person skilled in the art to which it pertains, or with which it is most nearly connected, to make and use the same.

EXAMPLE 7

Below is disclosed the amino acid sequence of FGF-20.

(SEQ ID NO:1)

```
Met Ala Pro Leu Ala Asp Val Gly Thr Phe Leu Gly Gly Tyr Asp Ala
(SEQ ID NO:1)
 1               5                  10                  15

Leu Gly Gln Val Gly Ser His Phe Leu Leu Pro Pro Ala Lys Asp Ser
             20                  25                  30

Pro Leu Leu Phe Asn Asp Pro Leu Ala Gln Ser Glu Arg Leu Ser Arg
             35                  40                  45

Ser Ala Pro Ser Asp Leu Ser His Leu Gln Gly Ile Leu Arg Arg Arg
     50                  55                  60

Gln Leu Tyr Cys Arg Thr Gly Phe His Leu Gln Ile Leu Pro Asp Gly
 65                  70                  75                  80

Asn Val Gln Gly Thr Arg Gln Asp His Ser Arg Phe Gly Ile Leu Glu
                 85                  90                  95

Phe Ile Ser Val Ala Ile Gly Leu Val Ser Ile Arg Gly Val Asp Thr
                100                 105                 110

Gly Leu Tyr Leu Gly Met Asn Asp Lys Gly Glu Leu Phe Gly Ser Glu
            115                 120                 125

Lys Leu Thr Ser Glu Cys Ile Phe Arg Glu Gln Phe Glu Glu Asn Trp
    130                 135                 140

Tyr Asn Thr Tyr Ser Ser Asn Leu Tyr Lys His Gly Asp Ser Gly Arg
145                 150                 155                 160

Arg Tyr Phe Val Ala Leu Asn Lys Asp Gly Thr Pro Arg Asp Gly Thr
                165                 170                 175

Arg Ala Lys Arg His Gln Lys Phe Thr His Phe Leu Pro Arg Pro Val
                180                 185                 190

Asp Pro Glu Lys Val Pro Glu Leu Tyr Lys Asp Leu Met Gly Tyr Ser
                195                 200                 205
```

---

What is claimed is:

1. A method of treating a hyperphosphatemic condition in a mammal, said method comprising administering to a mammal afflicted with the disorder a therapeutically effective amount of an isolated polypeptide comprising the amino acid sequence of SEQ ID NO:1.

2. The method of claim 1, wherein, the isolated polypeptide consists of the amino acid sequence of SEQ ID NO:1.

3. The method of claim 1, wherein said mammal has a serum phosphate level greater than 5.0 mg/dL.

4. The method of claim 1, wherein said isolated polypeptide is administered by intravenous injection.

5. A method of treating a condition involving deposition of calcium and phosphate in the arteries or soft tissues of a mammal, said method comprising administering to said mammal a therapeutically effective amount of an isolated polypeptide comprising the amino acid sequence of SEQ ID NO:1.

6. The method of claim 5, wherein, the isolated polypeptide consists of the amino acid sequence of SEQ ID NO:1.

7. The method of claim 5, wherein said mammal has a serum phosphate level greater than 5.0 mg/dL.

8. The method of claim 5, wherein said isolated polypeptide is administered by intravenous injection.

9. The method of claim 5, wherein said soft tissue is muscle tissue.

* * * * *

SEQUENCE LISTING

<160> NUMBER OF SEQ ID NOS: 1

<210> SEQ ID NO 1
<211> LENGTH: 208
<212> TYPE: PRT
<213> ORGANISM: Homo sapiens

<400> SEQUENCE: 1

```
Met Ala Pro Leu Ala Asp Val Gly Thr Phe Leu Gly Gly Tyr Asp Ala
 1               5                  10                  15

Leu Gly Gln Val Gly Ser His Phe Leu Leu Pro Pro Ala Lys Asp Ser
             20                  25                  30

Pro Leu Leu Phe Asn Asp Pro Leu Ala Gln Ser Glu Arg Leu Ser Arg
             35                  40                  45

Ser Ala Pro Ser Asp Leu Ser His Leu Gln Gly Ile Leu Arg Arg Arg
     50                  55                  60

Gln Leu Tyr Cys Arg Thr Gly Phe His Leu Gln Ile Leu Pro Asp Gly
 65                  70                  75                  80

Asn Val Gln Gly Thr Arg Gln Asp His Ser Arg Phe Gly Ile Leu Glu
                 85                  90                  95

Phe Ile Ser Val Ala Ile Gly Leu Val Ser Ile Arg Gly Val Asp Thr
```

-continued

```
            100                 105                 110
Gly Leu Tyr Leu Gly Met Asn Asp Lys Gly Glu Leu Phe Gly Ser Glu
        115                 120                 125

Lys Leu Thr Ser Glu Cys Ile Phe Arg Glu Gln Phe Glu Glu Asn Trp
        130                 135                 140

Tyr Asn Thr Tyr Ser Ser Asn Leu Tyr Lys His Gly Asp Ser Gly Arg
145                 150                 155                 160

Arg Tyr Phe Val Ala Leu Asn Lys Asp Gly Thr Pro Arg Asp Gly Thr
                165                 170                 175

Arg Ala Lys Arg His Gln Lys Phe Thr His Phe Leu Pro Arg Pro Val
            180                 185                 190

Asp Pro Glu Lys Val Pro Glu Leu Tyr Lys Asp Leu Met Gly Tyr Ser
        195                 200                 205
```